(12) United States Patent
Poirier et al.

(10) Patent No.: US 8,419,771 B2
(45) Date of Patent: Apr. 16, 2013

(54) IMPLANTABLE SPINAL FIXATION CROSSLINK

(75) Inventors: David A. Poirier, El Dorado Hills, CA (US); Robert A. Rovner, Danville, CA (US); Barry L. Shevick, Fair Oaks, CA (US)

(73) Assignee: Partnership of David A. Poirier and Robert A. Rovner, Danville, CA (US)

( * ) Notice: Subject to any disclaimer, the term of this patent is extended or adjusted under 35 U.S.C. 154(b) by 1126 days.

(21) Appl. No.: 12/077,596

(22) Filed: Mar. 17, 2008

(65) Prior Publication Data

US 2009/0234390 A1 Sep. 17, 2009

(51) Int. Cl.
*A61B 17/70* (2006.01)

(52) U.S. Cl.
USPC .......................................... 606/250; 606/246

(58) Field of Classification Search ........... 606/246–279
See application file for complete search history.

(56) References Cited

U.S. PATENT DOCUMENTS

| | | | |
|---|---|---|---|
| 5,330,473 A | 7/1994 | Howland | |
| 5,601,554 A | 2/1997 | Howland | |
| 5,667,507 A | 9/1997 | Corin | |
| 5,676,665 A | 10/1997 | Bryan | |
| 5,707,372 A | 1/1998 | Errico | |
| 5,709,684 A | 1/1998 | Errico | |
| 5,752,955 A | 5/1998 | Errico | |
| 5,947,965 A | 9/1999 | Bryan | |
| 6,139,548 A | 10/2000 | Errico | |
| 6,238,396 B1 | 5/2001 | Lombardo | |
| 6,485,491 B1 | 11/2002 | Farris | |
| 6,524,310 B1 | 2/2003 | Lombardo | |
| 7,104,993 B2 | 9/2006 | Baynham | |
| 7,122,036 B2 | 10/2006 | Vanacker | |
| 2001/0047171 A1 | 11/2001 | Troxell | |
| 2003/0004512 A1* | 1/2003 | Farris et al. ..................... | 606/61 |
| 2003/0114853 A1 | 6/2003 | Burgess | |
| 2005/0080416 A1* | 4/2005 | Ryan et al. ....................... | 606/61 |
| 2005/0090821 A1 | 4/2005 | Berrevoets | |
| 2005/0228377 A1 | 10/2005 | Chao | |
| 2006/0009766 A1 | 1/2006 | Lee | |
| 2006/0064091 A1* | 3/2006 | Ludwig et al. .................. | 606/61 |
| 2006/0064093 A1 | 3/2006 | Thramann | |
| 2006/0241598 A1 | 10/2006 | Khalili | |
| 2006/0271045 A1 | 11/2006 | Hubbard | |
| 2006/0271051 A1 | 11/2006 | Berrevoets | |
| 2007/0016197 A1* | 1/2007 | Woods et al. .................... | 606/61 |
| 2008/0215094 A1* | 9/2008 | Taylor ........................... | 606/246 |

FOREIGN PATENT DOCUMENTS

EP 1857064 11/2007

* cited by examiner

*Primary Examiner* — Eduardo C Robert
*Assistant Examiner* — Nicholas Plionis
(74) *Attorney, Agent, or Firm* — Heisler & Associates (57) ABSTRACT

A crosslink is provided for joining two spine rods. The crosslink includes an elongate tie rod and a pair of housings at each end of the tie rod. The housings are preferably identical and have independent fasteners including a spine rod fastener and a tie rod fastener for connecting each housing to one of the spine rods and fixation of the tie rod. The tie rod fasteners include a pair of hemisphere clamps residing within a chamber in the housing which grip the tie rod therebetween to fix the tie rod to the clamp when a set screw applies a clamping force on the hemisphere clamps. The tie rod fastener is adjustable, so that both translation of the tie rod relative to the housings and rotation about three mutually perpendicular axes can be accommodated for orienting of the housings relative to the tie rod precisely where desired.

8 Claims, 4 Drawing Sheets

IMPLANTABLE SPINAL FIXATION CROSSLINK

FIELD OF THE INVENTION

The following invention relates to implantable medical devices for coupling adjacent vertebrae of a spine together and strengthening and supporting the spine. More particularly, this invention relates to crosslinks for such implantable spinal fixation devices which generally include rods on opposite sides of the spine coupled through pedicle screws or other attachments directly to the vertebrae, with the crosslink securing the two rods to each other.

BACKGROUND OF THE INVENTION

For certain spine injuries, the use of an implantable spinal fixation device is indicated to join two or more vertebrae together. A common form of spinal fixation includes utilizing an elongate spinal rod oriented generally parallel to the spine and spaced laterally to one side of the spine. This rod is coupled to at least two vertebrae, and often more than two vertebrae, through various different fixation fasteners. One common form of fixation fastener is a pedicle screw which is screwed directly into the pedicle of each vertebrae. These pedicle screws have portions thereof which can be secured to the rod.

Typically, two spinal rods are provided on opposite sides of the spine with at least two pedicle screws on each rod. The resulting arrangement secures the two vertebrae together while maintaining spacing between the vertebrae and transferring vertical loads along the spinal rod, rather than directly between the vertebrae, so that damaged vertebrae can still function by passing vertical loads through this spinal fixation device.

Often it is beneficial for these two spine rods to be coupled together to prevent relative motion therebetween, or to at least limit such relative motion. Crosslinks are known in the prior art which act as mechanical couplings to secure the two spine rods together. Such crosslinks generally include fasteners which allow them to be fastened to the rod on each end of the crosslink. Because the orientation of the two rods relative to each other as well as the distance between the rods can vary significantly, various different crosslinks have been designed which include adjustability features so that the crosslinks can secure the two rods together in a variety of different configurations and still provide a rigid link between the two spine rods once the crosslink has been fixed in place.

Such adjustable crosslinks known in the prior art are exemplified by crosslinks and related structures disclosed in U.S. Pat. Nos. 5,330,473, 5,601,554, 5,667,507, 5,676,665, 5,707, 372, 5,709,684, 5,752,955, 5,947,965, 6,139,548, 6,238,396, 6,485,491, 6,524,310, 7,104,993 and 7,122,036 and U.S. Published Patent Application Nos. 2003/0004512, 2003/0114853, 2005/0090821, 2005/0228377, 2006/0064093, 2006/0241598, 2006/0271045 and 2006/0271051. These prior art crosslinks have been less than entirely adequate in that they either do not provide a high degree of adjustability to easily fit all potential different spine rod relative orientations, or they are not easily adjusted or used by the surgeons in the surgical setting.

In some instances a surgeon will even choose not to utilize any crosslink because known crosslinks have been too difficult to fix in place or provide insufficient additional stability to the overall spinal fixation implant to warrant the difficulty associated with their implantation. Furthermore, the spine itself can interfere with the crosslink by blocking a straight path between the two rods, making many such prior art crosslinks unable to fit as desired. Accordingly, a need exists for a crosslink which can join two spine rods of a spinal fixation system together which is easy for the surgeon to use and which is highly adjustable to provide the most preferred interconnection between the two spine rods.

SUMMARY OF THE INVENTION

With this invention a crosslink is provided for an implantable spinal fixation system which securely joins two spine rods together in a highly adjustable fashion. The crosslink includes an elongate tie rod with housings at either end of the tie rod. These housings can attach to the tie rod in a variety of different relative orientations. In particular, each housing includes a spine rod fastener independent of a tie rod fastener. The spine rod fastener secures the housing to the spine rod. The tie rod fastener which receives a head and a neck on one end of the tie rod within the housing and securely fastens the tie rod to the housing.

This tie rod fastener allows the head and neck of the tie rod to translate linearly relative to the housing, as well as rotate an orientation of the housing relative to the tie rod in three different directions about three mutually perpendicular axes. Thus, the orientation of the housing relative to the tie rod when fastened to the tie rod is adjustable in one or more of four different ways to cause the housing and tie rod to attach together in precisely the orientation desired for the tie rod.

With a housing at each end of the tie rod, and thus four degrees of freedom at each end of the tie rod, the surgeon has a large amount of freedom in positioning the crosslink precisely where desired before fixing the housings to the spine rods and to the tie rod to cause the crosslink to fix the two spine rods together.

The particular tie rod fastener within the housing preferably is in the form of a pair of hemisphere clamps within a chamber captured within the housing. The clamps are positioned on posterior and anterior sides of the neck of the tie rod. The chamber is configured to facilitate spherical rotation of these hemisphere clamps to a small degree. The hemisphere clamps have a hemi-cylindrical groove on flat faces thereof that receive the neck of the tie rod therein. A set screw clamps the two hemisphere clamps together and onto the neck of the tie rod. Before such tightening of the set screw, the tie rod can translate linearly along the hemi-cylindrical grooves of the hemisphere clamps, as well as the hemisphere clamps can rotate about three separate mutually perpendicular axes. When the set screw is then tightened, the rotational position of the tie rod relative to the housing becomes fixed.

The spine rod fastener of the housing is preferably in the form of a clamp nut which can be adjusted between a loose and a tight configuration relative to a groove adjacent thereto. The groove is sized and shaped to receive the spine rod therein when the clamp nut is loose. When the clamp nut is tightened, it tightens the spine rod within the groove to prevent movement of the spine rod relative to the housing. Both the clamp nut and set screw can be tightened by utilizing a rotational tool accessing each housing posteriorly. Thus, the crosslink can be generally put into position and then adjusted to a desirable position. As portions of the housings and tie rod are placed where desired, the surgeon utilizes a rotating tool to fix the different parts of the housing to either the spine rod or the tie rod. When all of the rotating elements have been tightened by the surgeon, the housings and tie rod can no longer move relative to each other or relative to the spine rods, so that the two spine rods are securely joined together by the crosslink.

OBJECTS OF THE INVENTION

Accordingly, a primary object of the present invention is to provide a crosslink for an implantable spinal fixation assembly that can secure the two spine rods together and prevent relative motion therebetween.

Another object of the present invention is to provide a crosslink which is adjustable in a variety of different ways to give the surgeon options for placement and orientation of the crosslink.

Another object of the present invention is to provide a crosslink which is easy to attach to a spine rod.

Another object of the present invention is to provide a crosslink which is easy to adjust in position and orientation.

Another object of the present invention is to provide a crosslink which has a high degree of strength and a large amount of clamping force onto the spine rods such that a very secure attachment of the two spine rods together is provided.

Another object of the present invention is to provide a crosslink which can join two spine rods together even when the portions of the spine between the two spine rods blocks a direct path between the two spine rods.

Another object of the present invention is to provide a crosslink which is bilaterally symmetrical, so that it can be attached two different ways with equal effectiveness, to avoid confusion in surgical implantation and to simplify efforts in linking the crosslink to the spine rods.

Another object of the present invention is to provide a crosslink which has a pair of housings which are similar in form to simplify manufacture of various different subcomponents of the crosslink.

Another object of the present invention is to provide a crosslink which has anterior and posterior clamps for fixation to a tie rod which are similar in form so that they can be manufactured as a single item and reduce the possibility of improper assembly and minimize complexity of the crosslink.

Another object of the present invention is to provide a crosslink which has a configuration which exhibits a high strength when formed of biocompatible materials such as stainless steel, titanium alloys, or high strength plastic or composite materials.

Other further objects of the present invention will become apparent from a careful reading of the included drawing figures, the claims and detailed description of the invention.

DESCRIPTION OF THE PREFERRED EMBODIMENT

Referring to the drawings, wherein like reference numerals represent like parts throughout the various drawing figures, reference numeral 10 is directed to a crosslink for joining two spinal fixation assemblies 2 (FIGS. 1 and 2) on either side of a spine S. The fixation assemblies 2 generally include a spine rod R rigidly joined to the spine S through pedicle screws P or other attachment mechanisms. The spine rods R thus provide support for the spine S to help the spine S to support longitudinal loads experienced by the spine S. The crosslink 10 is rigidly coupleable to each of the spine rods R and spanning the spine S laterally, to rigidly join the two rods R and thus the two fixation assemblies 2 securely together.

In essence, and with particular reference to FIGS. 1-3 and 16, basic details of the crosslink 10 are described, according to a preferred embodiment. The crosslink 10 includes an elongate tie rod 20 and a pair of housings 30, with one housing 30 on each end of the tie rod 20. The housings 30 each include a spine rod R fastener for securing the housings 30 to one of the spine rods R, and a tie rod 20 fastener for fixing each of the housings 30 to one of the ends of the tie rod 20. In particular, the housings 30 include a clamp nut 50 movable relative to a groove 35 that can receive one of the rods R therein. The clamp nut 50 of each housing 30 captures the rod R within the groove 35 and secures the spine rods R to one of the housings 30. Clamp bolts 60 act on each of the clamp nuts 50 to move the clamp nuts 50 relative to the grooves 35 to capture the spine rods R therein.

The housings 30 also each include a bore 40 through which an end of the tie rods 20 can pass. The bore 40 extends into a chamber 42 which includes a pair of hemisphere clamps 70 on either side of the end of the tie rod 20 passing through the bore 40 and into the chamber 42. A set screw 80 compresses the hemisphere clamps 70 onto the end of the tie rod 20 within the chamber 42 to secure the end of the tie rod 20 to the housing 30.

The tie rod fasteners within each housing 30, including the hemisphere clamps 70 and set screw 80 can affix the housings 30 to ends of the tie rod 20 in a highly adjustable fashion, including adjustability about three separate mutually perpendicular axes and longitudinal translation between the housings 30 and the tie rod 20 along a long axis of the tie rod 20. Such adjustability allows the tie rod 20 to be positioned precisely as desired relative to the two housings 30. Once the set screws 80 are tightened, the housings 30 are fixed relative to the tie rod 20 so that the crosslink 10 can function as a rigid coupling between the two spine rods R.

More specifically, and with particular reference to FIGS. 1-3 and 9-11, details of the tie rod 20 of the crosslink 10 are described according to a preferred embodiment and two alternative embodiments. The tie rod 20 is an elongate rigid structure which provides primary structural strength to the crosslink 10 for securing the spine rods R together on opposite sides of the spine S. This tie rod 20 is preferably radially symmetrical about a long axis thereof so that the tie rod 20 can rotate about this long axis and present a similar geometry regardless of such rotation.

Figure 1:
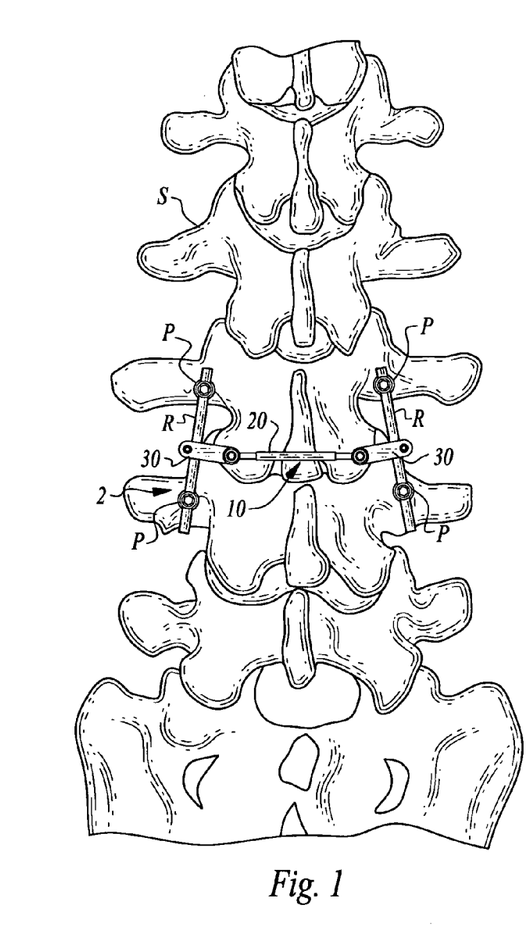
FIG. 1 is a posterior plan view of a human spine with fixation assemblies joining adjacent vertebrae together and with a crosslink fixing the two spine rods of the fixation assemblies together.

This long axis of the tie rod 20 is also referred to herein as the "X-axis" within a three dimensional set of Cartesian mutually perpendicular axes, arbitrarily provided to assist in defining the functional aspects of this invention. Other axes within this system include a "Y-axis" which is perpendicular to the X-axis and extends generally parallel with the spine S (upon implantation), and generally parallel with the spine rods R when implanted on the spine S (such as depicted in FIG. 1). A "Z-axis" is defined as an axis perpendicular to both the Y-axis and the X-axis and which extends in a posterior and anterior direction relative to the spine S (upon implantation).

Figure 9:
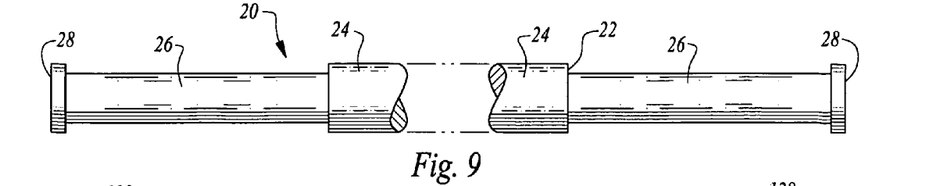
FIG. 9 is an elevation view of the tie rod of this invention, and with part of the central portion of the tie rod cut away to enlarge details for the ends of the tie rod.

The tie rod 20 includes an elongate rigid shaft 22 extending between ends of the tie rod 20. The tie rod 20 is preferably formed of a rigid biocompatible material such as a titanium alloy, stainless steel or appropriate biocompatible composites or plastic materials. A central portion 24 of the shaft 22 preferably has a somewhat greater diameter than two necks 26 adjacent each end of the tie rod 20. Heads 28 define terminal tips of the ends of the tie rod 20. These heads 28 preferably have a diameter similar to that of the central portion 24. The necks 26 thus define areas on the shaft 22 which have a slightly lesser diameter than other portions of the shaft 22. By making the central portion 24 slightly greater in diameter than the necks 26, this transition between the necks 26 and central portion 24 acts as a form of stop keeping the tie rod 20 from passing too far into the bore 40 within each of the housings 30.

Figure 3:
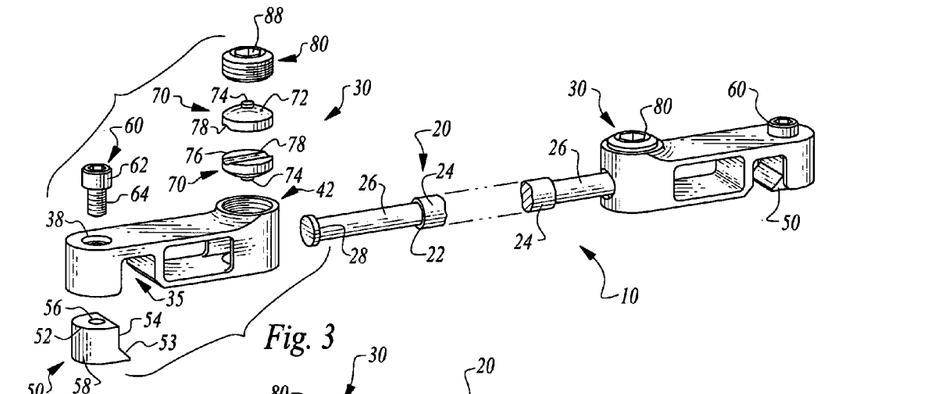
FIG. 3 is a perspective view of the crosslink of this invention showing two housings, one on each end of a tie rod, and with one of the housings having portions thereof exploded out to reveal interior details of the housing, but with both of the housings being identical in form.
Figures 4, 5, 6, 7, 8:
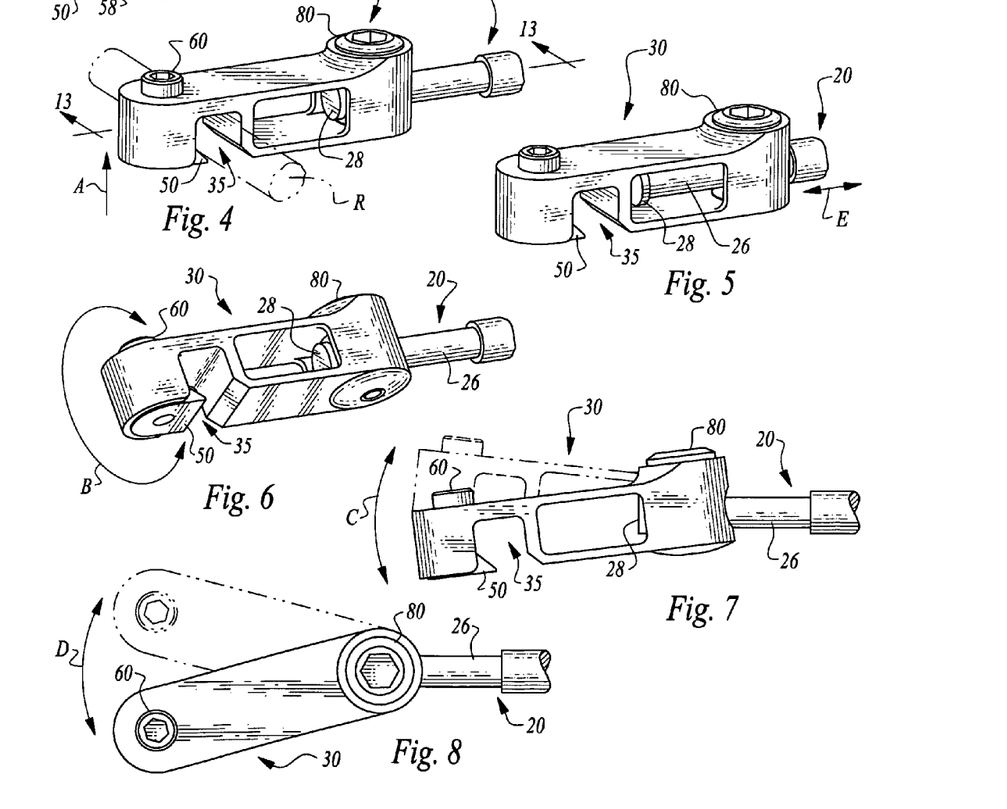
FIG. 4 is a perspective view of one of the housings and a portion of one of the tie rods and with a spine rod shown in broken lines captured within a groove in the housing for fixing the housing to the spine rod.
FIG. 5 is a perspective view similar to FIG. 4 but with the tie rod translating relative to the housing and illustrating one degree of freedom of the housing relative to the tie rod.
FIG. 6 is a perspective view similar to FIG. 5, but with the housing rotated about an axis colinear with a central axis of the tie rod, and illustrating a second degree of freedom of the housing relative to the tie rod.
FIG. 7 is a perspective view similar to FIG. 4, but with the housing rotating relative to the tie rod about an axis perpendicular to a long axis of the tie rod and illustrating a third degree of freedom of this invention.
FIG. 8 is a posterior plan view of a housing and portion of a tie rod of the crosslink of this invention and illustrating rotation of the housing relative to the tie rod about an axis perpendicular to the long axis of the tie rod and perpendicular to the axis of rotation shown in FIG. 7 and illustrating a fourth degree of freedom of this invention.

A length of the necks 26 between the heads 28 and the central portion 24 thus defines a maximum length of longitudinal translation, along the X-axis, for the tie rod 20 relative to the housings 30 (FIGS. 4 and 5). The heads 28 have a large enough diameter so that they can just barely fit through the bore 40, and so that the hemisphere clamps 70 (FIGS. 3 and 16) engage the heads 28 to keep the heads 28 from passing through the chamber 42 and out of the bore 40. In this way, the tie rod 20 remains captured to each of the housings 30 to avoid complete disassembly, while still allowing adjustment between the housings 30 and the tie rod 20. This tie rod 20 could have a constant diameter between the heads 28 if desired. Configured this way, translation into the bore 40 is constrained by the head 28 abutting portions of the housing 30 adjacent the groove 35. The bore 40 is sized large enough to accommodate tie rod 20 pivoting relative to the housing 30.

Figure 2:
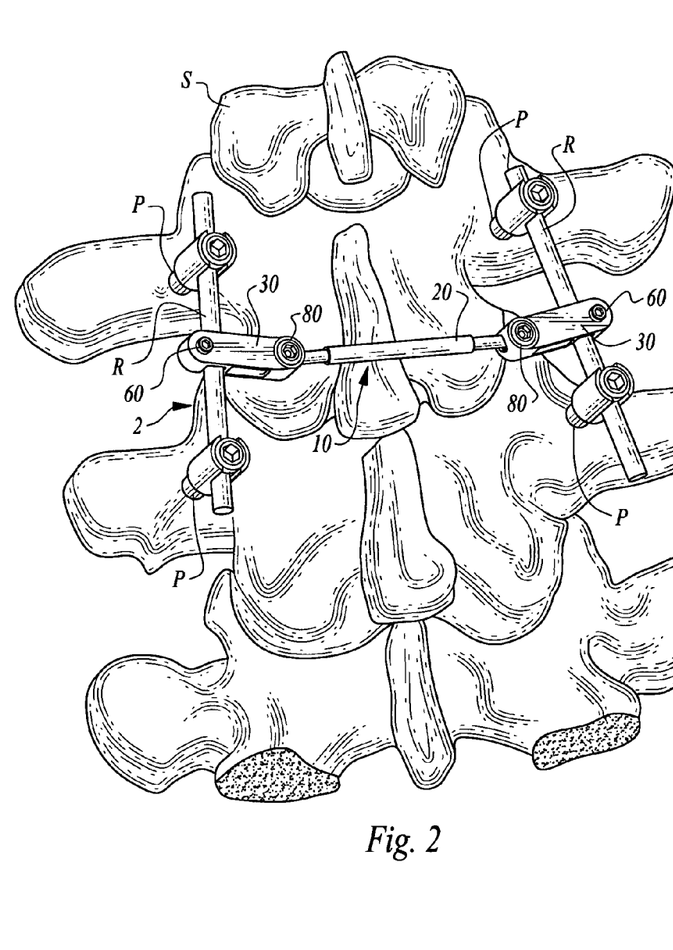
FIG. 2 is a perspective view similar to that which is shown in FIG. 1 and closer up to reveal additional detail.
Figure 10:
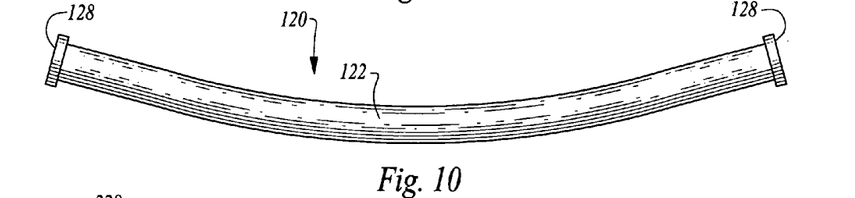
FIG. 10 is a front elevation view of a first alternative tie rod according to an alternative embodiment of this invention.
Figure 11:
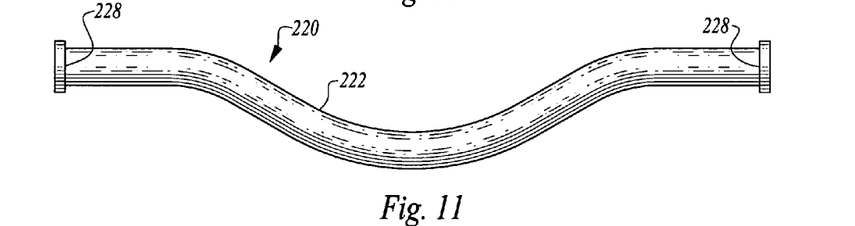
FIG. 11 is a front elevation view of a second alternative tie rod according to a second alternative embodiment of this invention.

With particular reference to FIGS. 10 and 11, two alternative tie rods 120, 220 are described which can be used in place of the tie rod 20 of the preferred embodiment (FIG. 9). With the first alternative tie rod 120 (FIG. 10), a curving shaft 122 is provided between two heads 128 at ends of the tie rod 120. Such a curving shaft 122 could have a constant diameter or have a greater diameter on a central portion separate from necks, similar to the tie rod 20 of the preferred embodiment (FIG. 9). By curving the first alternative tie rod 120, it can more effectively avoid interference with portions of the spine S that might block a straight path between the two spine rods R (FIGS. 1 and 2). Also, often the two spine rods R are not quite parallel to each other, but diverge slightly as they extend distally (toward the lower spine S) and converge slightly as they extend proximally (toward the upper spine S). By curving the first alternative tie rod 120 slightly, the heads 128 at the ends of the tie rod 120 are closer to perpendicular to the spine rods R, for maximum useful adjustability between the first alternative tie rod 120 and the housings 30 at each end of the tie rod 120.

The second alternative tie rod 220 exhibits a recurve shaft 222 extending between heads 228 at ends of the second alternative tie rod 220 (FIG. 11). This recurve shaft 222 has the benefit of a curve on a midpoint of the tie rod 220, but still keeps the heads 228 aligned axially with each other at the ends. Such a configuration provides the benefit of avoiding being blocked by portions of the spine S in a midpoint of the second alternative tie rod 220, while still maintaining the heads 228 at the ends of the tie rods 220 extending directly away from each other. In some instances, such a configuration may provide the greatest ease of use and flexibility in attachment of the housing 30 adjacent the ends of the tie rod 220, particularly for surgical applications where the spine rods R are close to parallel to each other.

These alternative tie rods 120, 220 are configured for use with the housings 30 similar to the tie rod 20, so that only one form of housing 30 need be provided. Thus, the potential is created that a kit could be provided with common housings, but tie rods of different shapes. A surgeon could then select a tie rod having a desired shape and then attach housings to the tie rod (or they could be pre-attached). Multiple different crosslinks 10 having different tie rods 20, 120, 220 could be preassembled before surgery, and then the surgeon would be able to select the crosslink 10 having the tie rod 20, 120, 220 having the most preferred shape for the particular surgical application. Note that tie rods can rotate about the X-axis freely. Thus, any bend therein can be aligned as desired, even after the housings 30 have been affixed to the spine rods R.

As another alternative, the tie rod 20, 120, 220 could be formed of a material which is sufficiently formable so that with appropriate tools (or by hand), the surgeon could custom bend the tie rod 20, 120, 220 to have a desired shape. Most preferably, the tie rod 20, 120, 220 would be sufficiently strong that a tool would be required for such bending. In this way, the tie rods 20, 120, 220 would avoid undesirable bending once implanted and affixed to spine rods R.

With particular reference to FIGS. 3 and 12-16, particular details of the housings 30 coupled to each end of the tie rod 20 are described, according to the preferred embodiment. These housings 30 are preferably identical in form in every respect. This makes the overall crosslink 10 substantially bilaterally symmetrical (other than the pitch of threaded surfaces) and reversible and reduces the number of parts which must be utilized to form the crosslink 10. The housings 30 are described below as a single unit, it being understood that two identical such housings 30 are provided at each end of the tie rod 20.

Figures 12, 13:
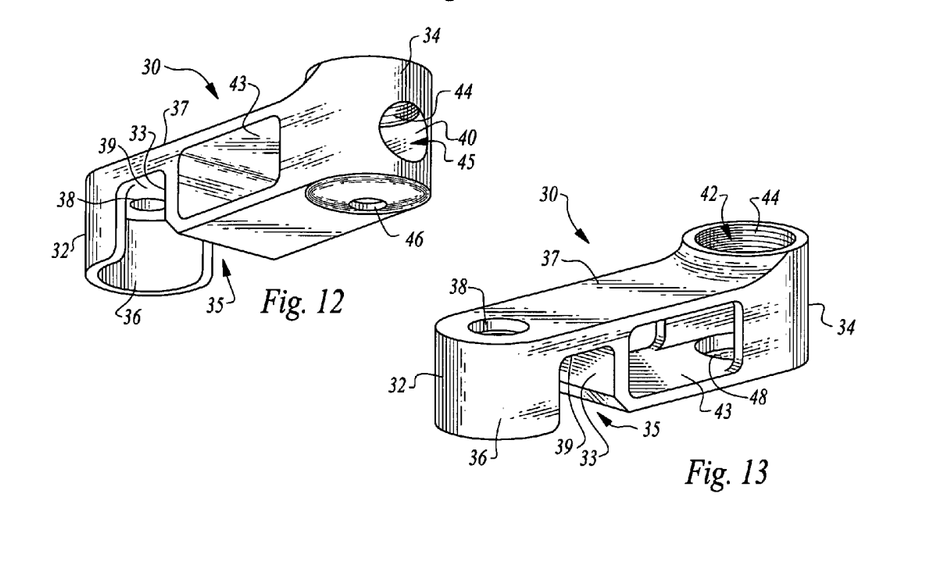
FIG. 12 is a perspective view of one of the housings of the crosslink of this invention with a clamp nut, hemisphere clamps and set screw removed, so that the monolithic shell of the housing can best be seen.
FIG. 13 is a perspective view similar to that which is shown in FIG. 12, but from a different perspective.

The housing 30 is a rigid unitary mass of material, typically the same material forming the tie rod 20, such as a titanium alloy, stainless steel, biocompatible composite materials or biocompatible plastic materials. The housing 30 includes a spine rod R fastener and a tie rod 20 fastener therein. These fasteners are independent of each other so that the spine rod R fastener can be attached first or the tie rod 20 fastener can be attached first. The surgeon thus has flexibility in both adjusting and fixing the housing 30 to the tie rod 20 to configure the crosslink 10 as desired at the implantation site.

The housing 30 includes a variety of different cavities and surfaces to support the spine rod R fastener and the tie rod 20 fastener. In particular, the housing 30 is somewhat elongate in form having a lateral end 32 and a medial end 34. The lateral end 32 is located most distant from the tie rod 20 and is configured with the spine rod R fastener thereon. The lateral end 32 includes a cavity beneath a top wall 37 defined by a side wall 33, a roof 39 and a shroud 36. Side wall 33 is a generally planar surface substantially perpendicular to the X-axis. The roof 39 is a substantially planar surface oriented perpendicular to the Z-axis and perpendicular to the side wall 33. The roof 39 is parallel with and spaced below the top wall 37 of the housing 30. The shroud 36 is spaced from the side wall 33 and extends down from the roof 39 (parallel to the Z-axis). The shroud 36 is thus somewhat parallel with the side wall 33. A groove 35 is provided as a space adjacent the side wall 33 and between the side wall 33 and the shroud 36, and below the roof 39. The groove 35 receives the spine rod R therein when the housing 30 is attached to the spine rod R.

Figures 14, 15, 16:
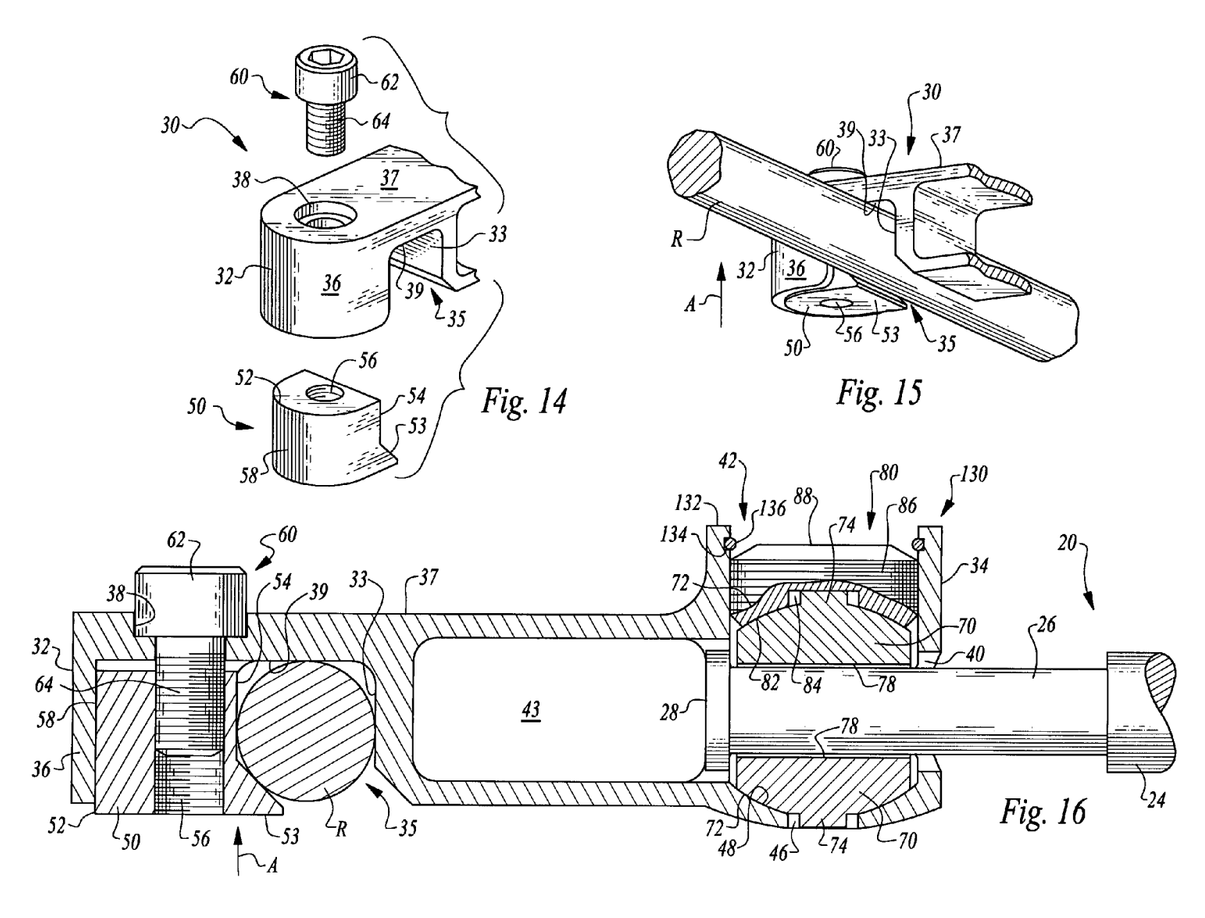
FIG. 14 is a perspective exploded view of a spine rod fastener portion of the housing of this invention, and illustrating how the clamp nut and clamp bolt pass through the housing and work with a groove to capture a spine rod therein.
FIG. 15 is a perspective view showing the same portion of the housing as FIG. 14, and with a rod shown therein captured by the clamp nut and clamp bolt.
FIG. 16 is a full sectional view of one of the housings of this invention, taken along the line 13-13 of FIG. 4 and revealing interior details of the housing, and with some portions of the housing altered to represent a first alternative housing including details for capturing of the set screw so the set screw cannot become inadvertently separated from the housing.

The clamp nut 50 is sized to fit within the cavity adjacent the shroud 36 and beneath the roof 39. the clamp nut 50 has a body 52 sized to fit inboard of the shroud 36. The body 52 includes a flat side 54 facing the side wall 33 and spaced from the side wall 33 by the groove 35. This flat side 54 is preferably substantially planar and parallel with the side wall 33. A beveled rise 53 is provided on a portion of the flat side 54 most distant from the roof 39. This beveled rise 53 is closer to the side wall 33 than other portions of the clamp nut 50 and acts to capture the spine rod R within the groove 35 when the clamp nut 50 is tightened.

A curving side 58 is provided on the clamp nut 50 opposite the flat side 54. This curving side 58 is sized and shaped to fit within the shroud 36. The curving side 58 has an only slightly lesser radius of curvature than the shroud 36, so that the curving side 58 and shroud 36 act together to keep the clamp nut 50 from significant rotation. Rather, when the clamp nut 50 is located beneath the roof 39 and adjacent the shroud 36, the clamp nut 50 is prevented from any movement other than movement along the Z-axis toward and away from the roof 39 (along arrow A of FIGS. 4, 15 and 16). The clamp nut 50 is preferably formed of a common material as that forming the housing 30.

When the spine rod R is located within the groove 35, the clamp nut 50 can be drawn upward toward the roof 39 until the beveled rise 53 of the clamp nut 50 impacts the spine rod R. Once such impact occurs, because the beveled rise 53 has a beveled form, the spine rod R is caused to be pressed both against the side wall 33 and roof 39, while also in contact with the beveled rise 53. These at least three points of contact (the flat side 54 might also be in slight contact with the spine rod R) distribute loads on the spine rod R to three locations of line contact, so that clamping compression forces are distributed over a relatively large surface area and a high degree of clamping force can be applied to the spine rod R without distorting the clamp nut 50, the groove 39 or the side wall 33 appreciably, and so that a very secure fastening of the housing 30 to the spine rod R is achieved without damaging stress concentrations at points of contact with the spine rod R.

A clamp bolt 60 is preferably provided to apply forces on the clamp nut 50 to draw the clamp nut 50 toward and away from the roof 39 (along arrow A). In particular, the clamp bolt 60 includes a head 62 and a threaded shaft 64 extending down from the head 62. The clamp nut 50 includes a threaded hole 56 therein which extends (parallel to the Z-axis) between the flat side 54 and the curving side 58 of the clamp nut 50. The housing 30 includes a stepped hole 38 extending down (parallel to the Z-axis) from the top wall 37 to the roof 39.

This stepped hole 38 has a step therein with portions above the step having a diameter at least as great as that of the head 62 of the clamp bolt 60 and portions of the stepped hole 38 below the step having a lesser diameter than that of the head 32, and as least as great as that of the threaded shaft 64. The clamp bolt 60 can pass into the stepped hole 38 and pass entirely through the housing 30 and into the cavity below the roof 39. The threaded shaft 64 of the clamp bolt 60 has threads that are complemental with the threaded hole 56 of the clamp nut 50. Thus, the clamp bolt 60 can thread into the threaded hole 56.

Because the clamp nut 50 is prevented from rotation by the curving side 58 and shroud 36, when the clamp bolt 60 is rotated, the clamp nut 50 is caused to move up and down (along arrow A) along a line aligned with a central shaft of the clamp bolt 60, and generally following a line parallel with the Z-axis for the crosslink 10. Rotation of the bolt 60 causes the spine rod R fastener to engage and disengage the spine rod R. When the clamp nut 50 is very loose, the spine rod R can be slid into the groove 35. As the clamp bolt 60 is rotated, the clamp nut 50 is moved upward (along arrow A) (FIGS. 15 and 16) until the spine rod R is captured within the groove 35.

The housing 30 also includes the tie rod 20 fastener on a portion of the housing 30 spaced from the groove 35 and closer to the tie rod 20 and medial end 34 than to the groove 35. In particular, the housing 30 includes a bore 40 on the medial end 34 of the housing 30 and passing through the medial end 34 into a chamber 42 inside of the housing 30. The chamber 42 is also in communication with a central gap 43 of the housing 30. This central gap 43 defines a space between the side wall 33 and the chamber 42. The central gap 43 is preferably open on sides of the housing 30 below (parallel to the Z-axis) the top wall 37. Such openings allow the head 28 and neck 26 of the tie rod 20 to pass laterally out of the housing 30 slightly should the housing 30 be rotated (about the Z-axis) at a relatively high angle away from the X-axis in which the tie rod 20 is oriented.

The bore 40 is sized to receive one of the heads 28 of the tie rod 20 passing therethrough, and with the neck 26 adjacent the head 28 residing within the chamber 42, while the head 28 extends just past the chamber 42 and into the central gap 43 at least a small amount. The chamber 42 defines a space where the hemisphere clamps 70 are located, described in detail below. The chamber 42 is not only accessed by the bore 40, but also by a threaded upper end 44 extending up through a posterior side of the housing 30. This threaded upper end 44 is generally cylindrical in form and extends parallel to the Z-axis for the crosslink 10. The chamber 42 also includes a spherical floor 48 opposite the threaded upper end 44. This spherical floor 48 includes an alignment port 46 centrally located thereon to assist in restraining rotation of the hemisphere clamps 70 somewhat, as described in detail below. The threaded upper end 44 is large enough to allow the hemisphere clamps 70 to drop into the chamber 42 during installation and configuring of the tie rod 20 within the housing 30 to form the crosslink 10.

With particular reference to FIGS. 3 and 16, details of the hemisphere clamps 70 are described. The housing 30 preferably includes two identical hemisphere clamps 70. By forming the hemisphere clamps 70 identical to each other, they need not be kept in separate inventory and the simplicity of the housings 30 is increased. Each hemisphere clamp 70 includes a spherical surface 72 opposite a flat surface 76. A post 74 extends from the spherical surface 72 generally perpendicular to the flat surface 76. The flat surface 76 includes a hemi-cylindrical channel therein.

The spherical surface 72 is provided with a curvature similar to that of the spherical floor 48 in the chamber 42. The post 74 is sized to fit within the alignment port 46 in the spherical floor 48. The alignment port 46 is slightly larger in width than the post 74, so that the hemisphere clamp 70 below the tie rod 20 (on the anterior side) can rotate adjacent the spherical floor 48 somewhat and the post 74 can move within the alignment port 46 somewhat. The alignment port 46 helps to restrain the spherical surface of the hemisphere clamp 70 from rotating more than a maximum desired amount.

The hemi-cylindrical channel 78 has a radius similar to a radius of the necks 26 of tie rod 20. The hemi-cylindrical channel 78 extends about a central axis aligned with a central axis of the tie rod 20 when the tie rod 20 has a neck 26 resting within the hemi-cylindrical channel 78. The hemi-cylindrical channel 78 defines that portion of the hemisphere clamps 70 which engage the neck 26 of the tie rod 20.

One hemisphere clamp 70 is preferably located on the anterior side of the neck 26 and one hemisphere clamp 70 is preferably located on the posterior side of the neck 26. The two hemisphere clamps 70 can sandwich the neck 26 of the tie rod 20 therebetween to fix the tie rod 20 in position relative to the housing 30. The bore 40 is sized slightly larger than the neck 26 of the tie rod 20, both to allow installation of the tie rod 20 into the housing 30 by passing of the head 28 and neck 26 of the tie rod 20 through the bore 40 and also to facilitate the small amount of pivoting of the tie rod 20 relative to the housing 30, as described in detail below.

It is conceivable that only one hemisphere clamp 70 could be utilized, with the other clamp 70 replaced with a planar bearing surface or other fixed reference surface.

The set screw 80 fits within the threaded upper end 44 of the chamber 42 above the hemisphere clamps 70 on a posterior side thereof. The set screw 80 includes a concave face 82 adapted to abut the hemisphere clamp 70 on the posterior side of the neck 26 of the tie rod 20. The concave face 82 preferably has a spherical contour with a diameter similar to that of the spherical surface 72 of the hemisphere clamp 70. A blind bore 84 extends into the concave face 82. This blind bore 84 is preferably similar in form to the alignment port 46 in the chamber 42 to receive the post 74 of one of the hemisphere clamps 70 therein and allow the adjacent hemisphere clamp 70 to rotate somewhat relative to the concave face 82 of the set screw 80.

The set screw 80 also includes a threaded side wall 86 with threads complemental to the threads of the threaded upper end 44 of the chamber 42. A tool face 88 is provided on a side of the set screw 80 opposite the concave face 82. The tool face 88 is adapted to receive a tool therein which can rotate the set screw 80 to cause the set screw 80 to move up and down along the Z-axis (posteriorly and anteriorly) within the chamber 42 and threaded upper end 44 (parallel to arrow A of FIGS. 4, 15 and 16).

When the set screw 80 is rotated to move this set screw 80 down toward the hemisphere clamps 70, it compresses the two hemisphere clamps 70 against the tie rod 20 and against the spherical floor 48. Friction forces between the concave face 82 of the set screw 80 and the spherical surface 72 of the hemisphere clamp 70, as well as friction forces between the spherical surface 72 of the hemisphere clamp 70 and the spherical floor 48 all act to securely keep the hemisphere clamps 70 fixed in position and with the tie rod 20 therebetween fixed in position where they are presented when the set screw 80 is tightened down against the hemisphere clamp 70.

Both the set screw 80 and the clamp bolt 60 are oriented so that rotating standard threads in a clockwise direction will cause a tightening action for either spine rod R fastening or tie rod 20 fastening to the housing 30. Thus, a very logical direction of rotation is utilized by the surgeon for tightening or loosening the housing 30 to both the spine rod R and the tie rod 20. In particular, clockwise rotation for tightening and counterclockwise rotation for loosening. Such a direction of rotation is the same for both of the housings 30 on each end of the tie rod 20 (FIGS. 1 and 2). The surgeon thus has a very intuitive operation to perform for tightening the housings 30 to the spine rods R and the tie rod 20.

A first alternative housing 130 is depicted in FIG. 16. This first alternative housing 130 is similar to the housing 30 of other embodiments except that the threaded upper end 44 of the housing 30 of the embodiments of FIGS. 1-15 is extended with the alternative housing 130 to extend up to a rim 132 which extends further above the wall 37 than in embodiments of FIGS. 1-15. A raised rim 132 has an annular groove 134 formed therein above threads in the threaded upper end 44. A retainer ring 136 can reside within this annular groove 134. This retainer ring 136 would typically be snapped into place after placing of the set screw 80 within the threaded upper end 44 of the chamber 42. The retainer ring 136 prevents the set screw 80 from backing all the way out of the housing 30 and potentially becoming displaced relative to the housing 30.

If desired, the retainer ring 136 and annular groove 134 can be positioned so that the set screw 80 can only be loosened slightly on the tie rod 20, so that the tie rod 20 remains captured by the hemisphere clamps 70 within the housing 30. In this way, the single retainer ring 136 both keeps the set screw 80 within the housing 30 and keeps the end of the tie rod 20 within the housing 30 so that the housings 30 and tie rod 20 of the crosslink remain captured together even before tightening. This configuration eliminates even the possibility that small portions of the crosslink 10 might become displaced and potentially fall into the patient during a surgical procedure.

With particular reference to FIGS. 4-8, the four degrees of freedom of the crosslink 10 are described. In FIG. 4 a perspective view is shown of the housing at one end of the tie rod 20. The rod R is shown secured to the housing 30 through movement of the clamp nut 50 (along arrow A) and clamp bolt 60. As depicted in FIG. 4, the tie rod 20 has been secured to the housing 30 in a standard configuration with the tie rod 20 extending along the X-axis and with the housing 30 mounted with no rotation of either the X-axis, the Y-axis or the Z-axis, but rather positioned so that the tie rod 20 is precisely perpendicular to the spine rod R and in a common plane with the spine rod R.

With reference to FIG. 5, translation of the tie rod 20 axially along the X-axis (along arrow E of FIG. 5) is illustrated. The length of the neck 26 and the ability of the hemi-cylindrical grooves 78 and the hemisphere clamps 70 to allow sliding of the neck 26 of the tie rod 20 relative to the clamps 70 when the set screw 80 is loose, facilitates such translation along the X-axis. Translation along the Y-axis or the Z-axis is restrained by the hemisphere clamps 70, except that a very small amount of looseness between the hemisphere clamps 70 might be presented before tightening of the set screw 80. Such translation along arrow E allows a distance between the two spine rods R to vary and for a single crosslink 10 to be utilizable for spine rods R having different spacings from each other.

With particular reference to FIG. 6, rotation about the X-axis is illustrated between the housing 30 and the tie rod 20. The housing 30 can rotate, along arrow B, in either direction relative to the tie rod 20. Such rotation about the X-axis is particularly useful when the two spine rods R are not in a common plane, but rather skewed relative to each other. While a high degree of rotation about arrow B is possible, most preferably to maintain access to the head 62 of the clamp bolt 60 and the tool face 88 of the set screw 80, such rotation about the X-axis would typically be limited to perhaps no more than 15° or 30° in either direction.

With particular reference to FIG. 7, rotation about the Y-axis is illustrated along arrow C of FIG. 7. In particular, the hemisphere clamps 70 can rotate between the concave face 82 of the set screw 80 and above the spherical floor 48 of the chamber 42 to facilitate such rotation as depicted in FIG. 7 about the Y-axis. Such rotation can allow the tie rod 20 to be elevated slightly above a plane in which the spine rod R is located. Typically, such rotation about the Y-axis (and along arrow C of FIG. 7) is limited to a relatively small amount (i.e. plus or minus 5°) to keep the crosslink 10 close to a common plane with the fixation assemblies 2 including the spine rods R (FIGS. 1 and 2).

With particular reference to FIG. 8, rotation about a Z-axis is illustrated between the housing 30 and tie rod 20. In particular, FIG. 8 depicts rotation along arrow D which can facilitate coupling of the crosslink 20 to spine rods R when the spine rods R are diverging away from each other, such as depicted in FIGS. 1 and 2. The housings 30 end up attaching to the spine rods R securely and are rotated at a junction between the tie rods 20 and the hemispheric clamps 70 to accommodate such angling of the spine rods R. With extreme rotation and crosslink 10 shortening along the X-axis (arrow E of FIG. 5), the head 28 of the tie rod 20 may pass out of sides of the central gap 43. With such rotation about the Z-axis, various different relative diverging angles between the spine rods R can be accommodated.

With the degrees of freedom illustrated in FIGS. 4-8, a surgeon can merely loosen the clamp bolt 60 and the set screw 80, drop the crosslink 10 onto the spine rods R with each spine rod R residing within one of the grooves 35, hold the tie rod 20 and position the tie rod 20 precisely where desired for maximum effectiveness of the crosslink 10 and then proceed to tighten the clamp bolts 60 and set screws 80 in each housing 30. Once these clamp bolts 60 and set screws 80 have been tightened, the crosslink 20 is now an entirely rigid construct fixing the two spine rods R together on opposite sides of the spine S. If portions of the spine S interfere with the tie rod 20 during such installation, the surgeon can select a crosslink 10 including one of the alternative tie rods 120, 220 (FIGS. 10 and 11) to avoid interference with portions of the spine S.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A crosslink for fixing the position of two spine rods secured to opposing sides of a spine, the crosslink comprising in combination:

a tie rod;

two housings;

each said housing including a spine rod fastener adapted to adjustably fix said housing to one of the spine rods;

each said housing including a tie rod fastener adapted to adjustably fix each said housing to said tie rod;

said spine rod fastener is independent of said tie rod fastener;

wherein said tie rod fastener includes a bore passing into said housing, said bore sufficiently large to receive an end of said tie rod therein, said housing including at least one movable structure within said housing adapted to bear on said tie rod within said housing to secure said tie rod to said housing;

wherein said tie rod fastener includes said tie rod having a neck on each end thereof and a head on each end thereof, said heads further from a central portion of said tie rod than said necks;

said movable structure adapted to engage one of said necks of said tie rod and secure one of said necks of said tie rod within said housing; and wherein said movable structure includes a pair of hemispherical clamps, each said hemispherical clamp having a flat surface adjacent said neck of said tie rod, said flat surface including a hemi-cylindrical groove therein adapted to receive said neck of said tie rod therein, said hemispherical clamps including a spherical surface opposite said flat surface with a post extending from said spherical surface substantially perpendicular to said flat surface, said hemispherical clamps located within a chamber inside said housing accessed by said bore, said chamber having a threaded upper end which is accessible from out of said housing at a location spaced from said bore, said threaded upper end including a set screw therein having a threaded side wall and said set screw including a concave face with a blind bore in a center thereof, said blind bore adapted to receive said post of said spherical surface of one of said hemispherical clamps therein, said blind bore having a larger diameter than a diameter of said post, said concave face adapted to bear on said spherical surface of said hemispherical clamp when said set screw is rotated, causing said threaded side wall of said set screw to engage with said threaded upper end of said chamber to draw said set screw down into said chamber and against said hemispherical clamp.

2. The crosslink of claim 1 wherein said spine rod fastener includes a groove adapted to at least partially straddle one of the spine rods and a linearly adjustable closure adapted to translate relative to other portions of said housing to capture one of the spine rods within said groove.

3. The crosslink of claim 2 wherein said closure includes a clamp nut including a beveled surface having portions of said beveled surface closer to a side wall of said groove opposite said clamp nut by a distance less than a diameter of the spine rod, said clamp nut threadably coupled to said housing such that rotation of a clamp bolt relative to said housing and said clamp nut causes said clamp nut to move toward said housing and capture the spine rod within said groove.

4. The crosslink of claim 1 wherein said two housings are reversibly locatable on either end of said tie rod.

5. The crosslink of claim 1 wherein said crosslink is bilaterally symmetrical, with each of said housings being identical in form, and wherein said tie rod has ends which are similar to each other in form.

6. The crosslink of claim 1 wherein said tie rod is substantially rigid and non-linear with a curve at a midpoint thereof.

7. A crosslink for fixing the position of two spine rods secured to opposing sides of a spine, the crosslink comprising in combination:
   a tie rod;
   two housings;
   each said housing including a spine rod fastener adapted to adjustably fix said housing to one of the spine rods;
   each said housing including a tie rod fastener adapted to adjustably fix said housing to said tie rod;
   said tie rod fastener adapted to fix said housing to said tie rod at different angles about three mutually perpendicular axes;
   wherein said spine rod fastener is independent of said tie rod fastener;
   wherein said tie rod fastener includes a bore passing into said housing, said bore sufficiently large to receive an end of said tie rod therein, said housing including at least one movable portion within said housing adapted to bear on said tie rod within said housing to secure said tie rod to said housing;
   wherein said tie rod has necks on each end thereof and heads on each end thereof, said heads further from a central portion of said tie rod than said necks;
   said movable portion adapted to engage one of said necks of said tie rod and secure one of said necks of said tie rod within said housing;
   wherein said at least one movable portion includes at least one hemispherical clamp, said hemispherical clamp having a flat surface adjacent said neck of said tie rod, said flat surface including a hemi-cylindrical channel therein adapted to receive said neck of said tie rod therein; and
   wherein said hemispherical clamp includes a spherical surface opposite said flat surface with a post extending from said spherical surface substantially perpendicular to said flat surface, said hemispherical clamp located within a chamber inside said housing accessed by said bore, said chamber having a threaded upper end which extends out of said housing at a location spaced from said bore, said threaded upper end including a set screw therein having a threaded side wall and said set screw including a concave face with a blind bore in a center thereof, said blind bore adapted to receive said post of said spherical surface of said hemispherical clamp therein, said blind bore having a larger diameter than a diameter of said post, said concave face adapted to bear on said spherical surface of said hemispherical clamp when said set screw is rotated, causing said threaded side wall of said set screw to engage with said threaded upper end of said chamber to draw said set screw down into said chamber and against said hemispherical clamp.

8. The crosslink of claim 7 wherein said at least one movable portion includes two hemispherical clamps of similar form, one of said hemispherical clamps located above said tie rod within said chamber and one of said hemispherical clamps located below said tie rod within said chamber, said chamber including a spherical floor opposite said threaded upper end, said spherical floor having a radius substantially matching a radius of said hemispherical clamps, said spherical floor having an alignment port adapted to receive said post of one of said hemispherical clamps therein, while allowing movement of said post within said alignment port.

* * * * *